(12) United States Patent
Kirkaune

(10) Patent No.: US 8,686,745 B2
(45) Date of Patent: Apr. 1, 2014

(54) APPARATUS AND METHOD FOR MEASURING WATER CONTENT AND SALT CONCENTRATION IN A MULTIPHASE FLUID FLOW

(75) Inventor: Odd Jan Kirkaune, Skollenborg (NO)

(73) Assignee: FMC Kongsberg Subsea AS, Kongsberg (NO)

(*) Notice: Subject to any disclaimer, the term of this patent is extended or adjusted under 35 U.S.C. 154(b) by 812 days.

(21) Appl. No.: 12/733,995

(22) PCT Filed: Oct. 3, 2008

(86) PCT No.: PCT/NO2008/000350
§ 371 (c)(1),
(2), (4) Date: Sep. 10, 2010

(87) PCT Pub. No.: WO2009/045111
PCT Pub. Date: Apr. 9, 2009

(65) Prior Publication Data
US 2011/0006790 A1    Jan. 13, 2011

(30) Foreign Application Priority Data
Oct. 3, 2007 (NO) .................................. 20074992

(51) Int. Cl.
*G01R 27/26* (2006.01)
*G01R 27/08* (2006.01)
*G01N 27/22* (2006.01)
*G01N 33/28* (2006.01)

(52) U.S. Cl.
CPC .......... *G01N 27/223* (2013.01); *G01N 33/2888* (2013.01)
USPC .......................................... 324/664; 324/698

(58) Field of Classification Search
USPC ............... 324/658, 691, 698, 664, 713, 76.77
See application file for complete search history.

(56) References Cited

U.S. PATENT DOCUMENTS

| | | | | |
|---|---|---|---|---|
| 2,617,855 A | * | 11/1952 | Etheridge, Jr. | 324/620 |
| 3,430,130 A | * | 2/1969 | Schneider | 324/442 |
| 3,711,767 A | * | 1/1973 | Campbell et al. | 324/538 |
| 3,870,951 A | * | 3/1975 | Brown et al. | 324/689 |
| 3,883,799 A | * | 5/1975 | Ulyanov | 324/684 |
| 4,266,425 A | | 5/1981 | Allport | |
| 4,288,741 A | * | 9/1981 | Dechene et al. | 324/664 |
| 4,652,811 A | * | 3/1987 | Kwiat et al. | 324/696 |
| 4,654,598 A | * | 3/1987 | Arulanandan et al. | 324/354 |
| 4,727,311 A | * | 2/1988 | Walker | 324/640 |
| 4,902,961 A | | 2/1990 | De et al. | |
| 5,070,725 A | | 12/1991 | Cox et al. | |
| 5,272,444 A | | 12/1993 | Cox | |
| 5,483,172 A | | 1/1996 | Radford | |
| 6,601,461 B2 | | 8/2003 | Maxit et al. | |
| 6,703,847 B2 | * | 3/2004 | Venter et al. | 324/663 |
| 7,541,817 B2 | * | 6/2009 | Nielsen et al. | 324/700 |
| 7,908,930 B2 | * | 3/2011 | Xie et al. | 73/861.04 |
| 2005/0210955 A1 | | 9/2005 | McCartan et al. | |

FOREIGN PATENT DOCUMENTS

EP          0 281 780 B1    3/1991
WO    WO 2007/018434 A1    2/2007

* cited by examiner

*Primary Examiner* — Paresh Patel

(57) ABSTRACT

An apparatus and a method are described for measuring water content and salt concentration in a multiphase fluid flow. A capacitive sensor (6, 7) is arranged in a pipe section (5) through which the multiphase fluid flow passes. A signal generator (10) is connected to the capacitive sensor (6, 7). A first measuring transducer (40) is adapted to measure a voltage across the capacitive sensor, and a second measuring transducer (50) is adapted to measure a current through the capacitive sensor. An output circuit (60) is adapted to generate output signals (70, 72) that indicate the salt concentration and water content in the multiphase fluid flow, based on signals emitted from the first (40) and the second (50) measuring transducer.

20 Claims, 4 Drawing Sheets

APPARATUS AND METHOD FOR MEASURING WATER CONTENT AND SALT CONCENTRATION IN A MULTIPHASE FLUID FLOW

TECHNICAL

The invention relates to an apparatus and a method for measuring water content and salt concentration in a multiphase fluid flow.

BACKGROUND OF THE INVENTION

There is a need for measuring water content and salt concentration in a multiphase fluid flow, especially in an installation for subsea petroleum production.

SUMMARY OF THE INVENTION

The invention is disclosed in the following claims.

DETAILED DESCRIPTION

Figure 1:
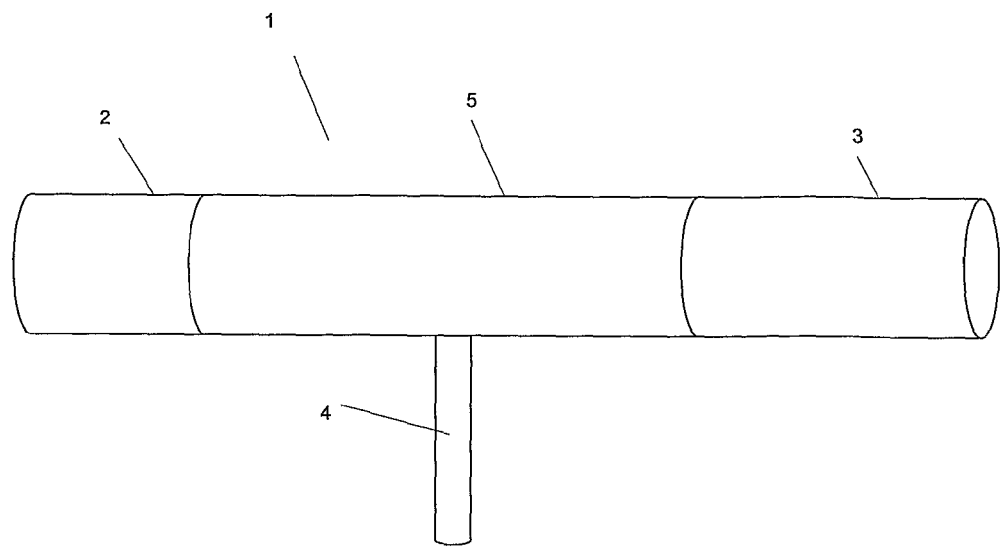
FIG. 1 is a schematic block diagram showing an assembly of pipe elements through which a multiphase fluid flow passes.

FIG. 1 is a schematic block diagram showing an assembly of pipe elements through which a multiphase fluid flow passes, especially in a subsea installation for petroleum production.

The multiphase fluid flow may, for example, comprise a phase of oil, such as crude oil, a water phase, where the water may have a certain salt content, and possibly a gas phase. The water content in such a multiphase fluid flow is often referred to by the term "water cut".

By way of example, in the case that the multiphase fluid flow passes through the assembly from left to right in the figure, the pipe element 2 represents a part of an upstream pipe arrangement, whilst the pipe element 3 represents a part of a downstream pipe arrangement. The intermediate pipe section 5, through which the multiphase fluid flow passes, constitutes a part of an apparatus for measuring water content and salt concentration in the multiphase fluid flow. The pipe section 5 comprises a capacitive sensor that is described in more detail below. Transverse to the pipe section 5, through the pipe wall, there is arranged an electrode duct 4.

It should be understood that the fluid flow may be in the opposite direction to that mentioned above.

Figure 2:
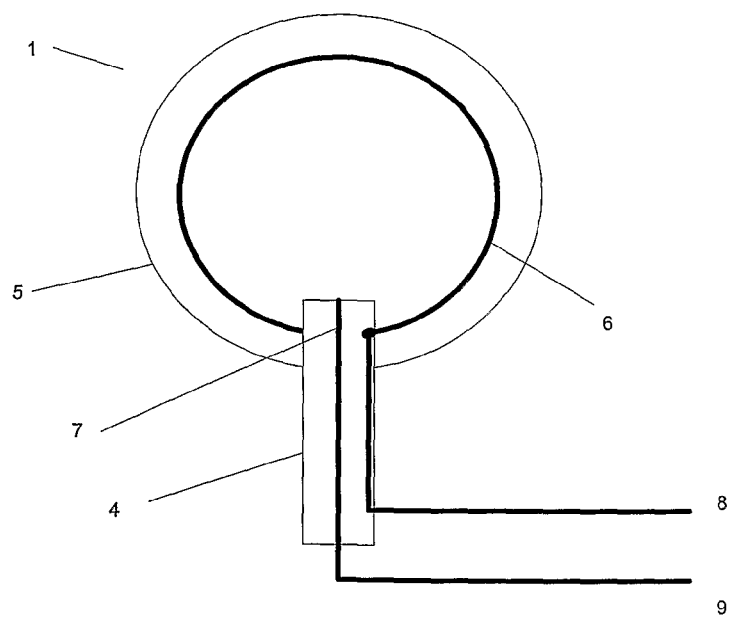
FIG. 2 is a schematic cross-sectional view of a pipe section through which the multiphase fluid flow passes.

FIG. 2 is a schematic cross-sectional view of the pipe section 5 through which the multiphase fluid flow passes. By way of example, a circular cross-section is illustrated for pipe section 5, but other cross-sectional shapes are possible.

Concentric with the wall of the pipe section 5, within the pipe wall, there is arranged a tubular or cylindrical first capacitive electrode 6 which extends along the whole, or only part of, the length of the pipe section 5. The multiphase fluid flow passes through the first capacitive electrode 6.

The first, capacitive electrode 6 is electrically connected to the first connection point 8 through an electric conductor.

A second, capacitive electrode 7 is also arranged in the fluid flow. As illustrated, the second capacitive electrode 7 is concentrated or punctiform, and is formed of the distal end of an electric conductor that runs through the electrode duct 4, perpendicular to the pipe section 5.

The second, capacitive electrode 7 is electrically connected to the second connection point 9 through an electric conductor.

In one embodiment, the second capacitive electrode 7 comprises a glass/metal seal penetrator. Such electrodes are used in subsea technology to provide a sealing which will withstand the operating conditions that prevail in subsea petroleum production, in particular high pressure.

The first 6 and the second 7 capacitive electrodes constitute a capacitive sensor with connection points 8, 9. It will be understood that the resulting electric properties for the capacitive electrode will vary according to, inter alia, the medium flowing in the multiphase fluid flow, including the salinity of the medium, and according to the flow rate, especially the rate of the medium's water component.

Figure 3:
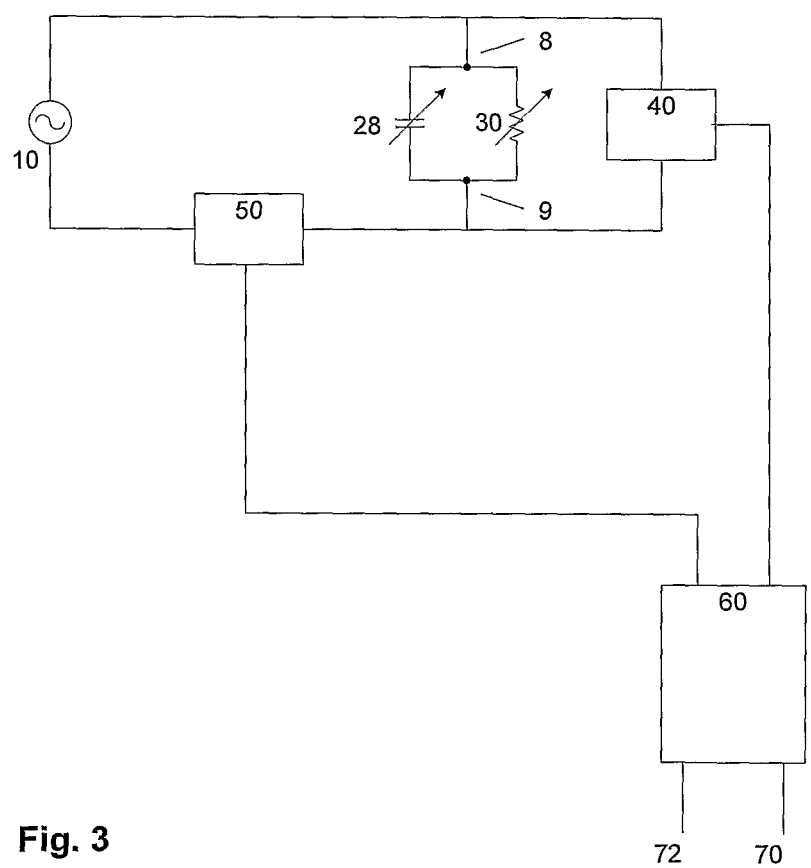
FIG. 3 is a schematic block diagram showing an apparatus for measuring water content and salt concentration in a multiphase fluid flow.

FIG. 3 is a schematic block diagram showing an apparatus for measuring water content and salt concentration in a multiphase fluid flow in a subsea installation for petroleum production.

In FIG. 3, between the points 8 and 9, there is illustrated a variable capacitance 28 and a variable resistance 30, connected in parallel. It should be understood that the parallel connection of the variable capacitance 28 and the variable resistance 30 is indicated to symbolise respectively the resulting capacitance and the resulting resistance for a capacitive electrode located i$_n$ a pipe section through which a multiphase fluid flow passes, such as the capacitive electrode described above with reference to FIGS. 1 and 2.

A signal generator 10 is connected to the capacitive sensor indicated at the points 8 and 9. The signal generator 10 is specially adapted to generate an RF signal with frequency in the range of 10 MHz to 2 GHz. In one embodiment the frequency range is 50 MHz to 125 MHz. The signal generator may be of the DDS type (Direct Digital Synthesizer).

In one embodiment, the signal generator may be controllable, as is further explained with reference to FIG. 4 below.

A first measuring transducer 40 is adapted to measure a voltage across the capacitive sensor, that is to say, the voltage between the points 8 and 9.

As illustrated, the signal generator is connected to the capacitive sensor through a second measuring transducer 50, which is adapted to measure the current that goes through the capacitive sensor. The second measuring transducer 50 is an ammeter, and can therefore ideally be regarded as a short-circuit, which has a minimum effect on the current therethrough.

The first measuring transducer 40 therefore emits a signal, for example, a voltage signal, which indicates the voltage across the capacitive sensor, whilst the second measuring transducer 50 emits a second signal, for example, a voltage signal, which indicates the current through the capacitive sensor. The first and the second signal are further connected to an output circuit 60, which is adapted to generate output signals 70, 72 that indicate the salt concentration and water content in the multiphase fluid flow, based on the signals emitted by the first measuring transducer 40 and the second measuring transducer 50.

For this purpose, the output circuit 60 in particular may be adapted to determine a phase difference between the signals emitted by the first 40 and the second 50 measuring transducer. The output circuit 60 can also be adapted to determine amplitude for the signal emitted by the second 50 measuring transducer.

Additional, possible details of the measuring transducers 40, 50 and the output circuit 60 are illustrated below with reference to FIG. 4.

Figure 4:
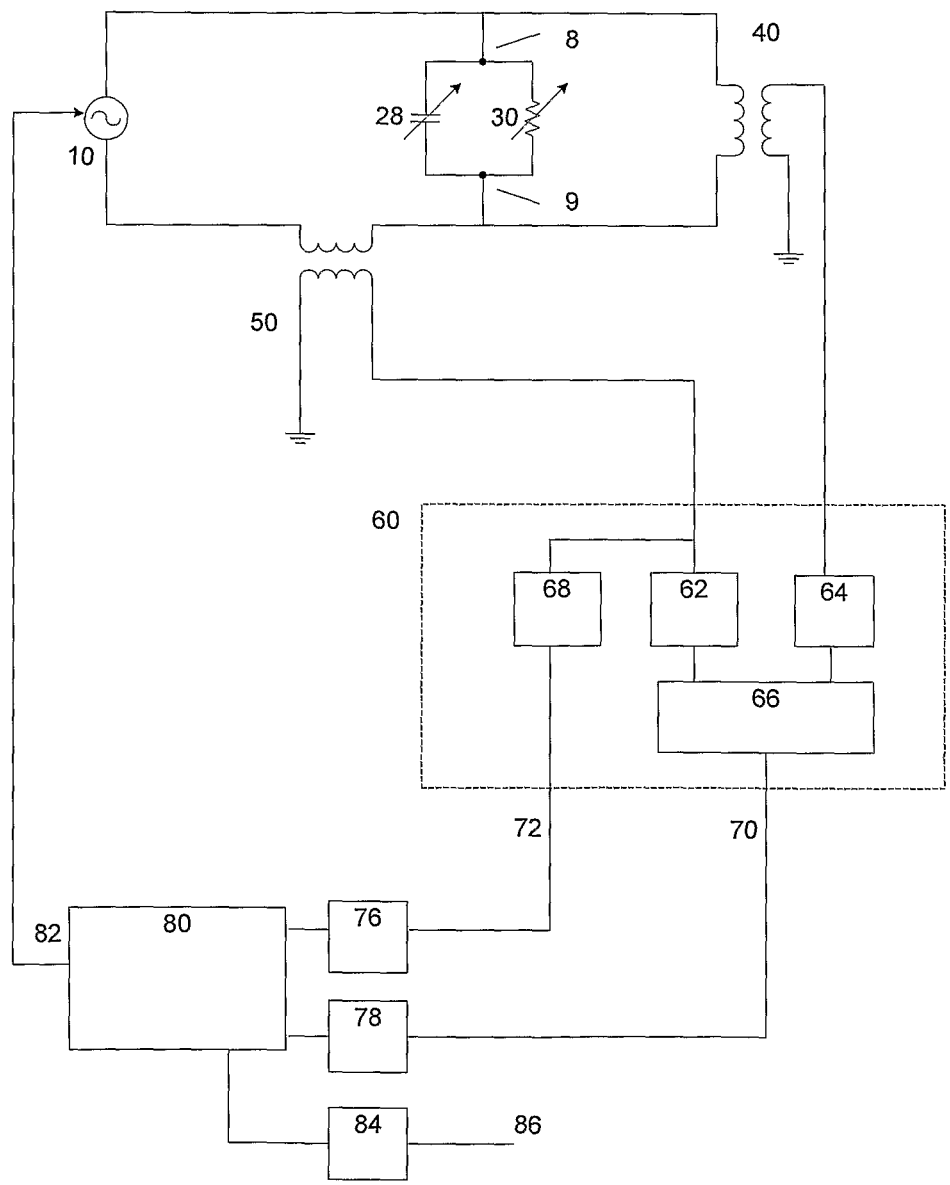
FIG. 4 is a schematic block diagram showing in more detail an apparatus for measuring water content and salt concentration in a multiphase fluid flow.

FIG. 4 is a schematic block diagram which shows in further detail an exemplary embodiment of an apparatus for measuring water content and salt concentration in a multiphase fluid flow in a subsea installation for petroleum production.

The embodiment illustrated in FIG. 4 corresponds largely to the embodiment in FIG. 3. The detailed description with reference to FIG. 3 therefore applies also as a description of the embodiment illustrated in FIG. 4, to the extent the two embodiments have common, identical or similar elements.

Specifically, FIG. 4 shows that the output circuit 60 in this exemplary embodiment can comprise two clipping amplifiers 62, 64, one for each signal emitted by the first measuring transducer 40 and the second measuring transducer 50. Each of the clipping amplifiers 62, 64 can be implemented as an amplifier with extremely high amplification, which therefore goes into saturation in the event of a small variation in input signal, for example, like a comparator which compares its input signal with a zero signal. It is thus ensured that the signal emitted from the clipping amplifiers 62, 64 has an at least approximately square wave form.

Furthermore, the output circuit 60 in this embodiment comprises a phase-sensitive demodulator 66, connected to respective outputs for the clipping amplifiers 62, 64. The demodulator 66 is adapted to emit a first output signal 70 wholly, substantially or approximately proportional to the phase difference between the two input signals fed to the demodulator. To achieve this, the demodulator 66, in an exemplary embodiment (not specifically illustrated), may comprise XOR port (exclusive-or-port), with its inputs connected to the respective outputs from the clipping amplifiers 62, 64. The pulse train generated by the XOR port can further be fed to a low-pass filter (not shown), which is also included in the demodulator 66. The low-pass filter has typically a corner frequency considerably smaller than the frequency for the signal from the signal generator 10. As an example, the corner frequency may be $1/10$ of the signal generator frequency, although other frequencies may be chosen. The output signal from the low-pass filter forms the first output signal 70 from the demodulator 66. This first output signal 70 represents the salt concentration in the multiphase fluid flow.

Furthermore, it is shown in FIG. 4 that the output circuit 60 in this embodiment comprises an amplitude detector 68, adapted to derive the amplitude of the signal that is emitted by the second measuring transducer 50. The amplitude detector emits a second output signal 72 which indicates the water content in the multiphase fluid flow. To achieve this, the amplitude detector, in an exemplary embodiment (not illustrated), comprises a rectifier and a low-pass filter. This low-pass filter also has typically a corner frequency substantially smaller than the frequency of the signal from the signal generator 10. As an example, the corner frequency may be $1/10$ of the signal generator frequency, although other frequencies may be chosen.

FIG. 4 also shows other possible details of the first measuring transducer 40 and the second measuring transducer 50.

As illustrated schematically, the first measuring transducer 40, in this exemplary embodiment, comprises a first transformer or inductive coupler, which provides a signal expressing the voltage measured across the capacitive sensor, and which is galvanically separated from the sensor. The first transformer comprises a primary winding that is connected in parallel to the capacitive sensor, that is to say, between the points 8 and 9. The first transformer further comprises a secondary winding, which on one side is connected to an electric reference point or neutral point/earth, and on the other side is connected to an input for the output circuit 60. The first transformer may further comprise a ferromagnetic core for magnetic coupling between the primary and the secondary winding.

The second measuring transducer 50 is, as illustrated schematically, a second transformer or inductive coupler. It comprises a primary winding that is connected to a connection point 9 on the capacitive sensor and the signal generator 10. The second transformer also comprises a secondary winding connected to an electric reference point or neutral point/earth on one side and to an input for the output circuit 60 on the other side. The second transformer may further comprise a ferromagnetic core for magnetic coupling between the primary and the secondary winding.

In the exemplary embodiment illustrated in FIG. 4 a control unit 80 is also shown, which comprises inputs connected via analog-digital converters 78, 76 to respectively the first output signal 70 and the second output signal 72. The control unit comprises a processing device such as a microprocessor, with associated memory for data and executable program, and suitable in-/out circuits, clock circuits etc. as can easily be selected by a person of skill in the art. The control unit 80 is adapted to input the first output signal 70 and the second output signal 72. The control unit is further configured to process values for the input signals. The control unit is further adapted to provide communication with an external communication bus 86, for example a serial communication bus of a type that complies with the RS485 specification, or a digital field bus such as a CAN-bus, or another type of communication solution suitable for subsea utilisation. To obtain such communication, a suitable communication adapter 84 is included.

The control unit 80 is in one embodiment further configured to emit a control signal 82 that is passed back to a control input for the signal generator 10. In this embodiment, the control unit 80 is further adapted to control certain signal parameters for the signal generator 10, especially frequency and amplitude for the signal that is generated by the signal generator 10.

The control unit 80 may also be configured to determine further derived values from the inputted first 70 and second 72 output signals. As an example, the control unit 80 can be configured for correlating water content (indicated by the first output signal 70) with the salt concentration (indicated by the second output signal 72) in order to determine salt concentration in the water phase (as distinct from salt concentration in the total multiphase flow)

Figure 5:
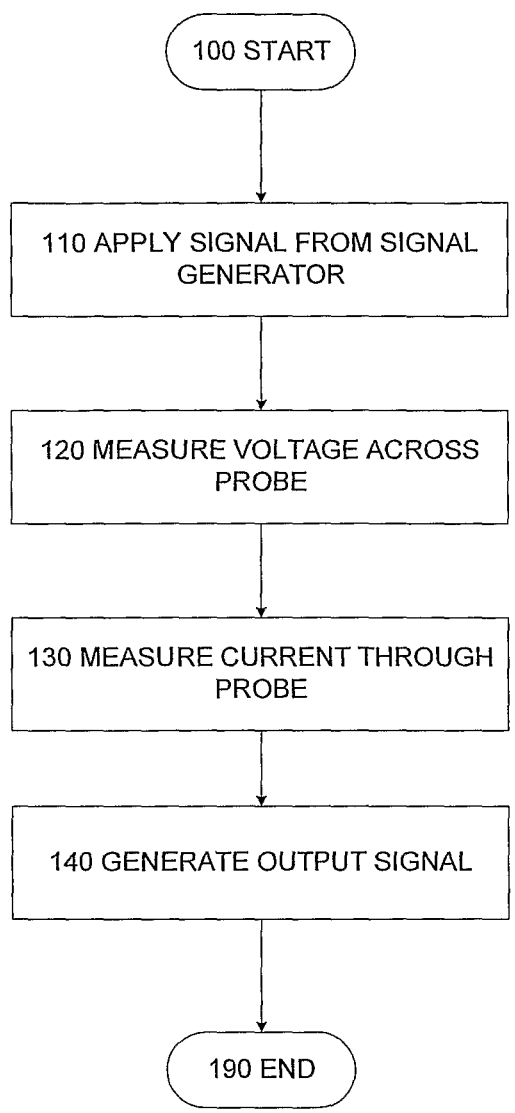
FIG. 5 is a schematic flow chart illustrating a method for measuring water content and salt concentration in a multiphase fluid flow.

FIG. 5 is a schematic flow chart illustrating a method for measuring water content and salt concentration in a multiphase fluid flow in a subsea installation for petroleum production.

The method starts with the initial step 100.

An application step 110 is first carried out to apply a signal from the signal generator 10 to a capacitive sensor located in a pipe section through which the multiphase fluid flow passes. The signal generator 10 generates a periodic signal, such as a sinus signal, as mentioned above.

A voltage measuring step 120 is then carried out, in which the voltage across the capacitive sensor is measured.

A current measuring step 130 is then carried out, in which the current through the capacitive sensor is measured.

It will be understood that the measuring steps 120 and 130 may be carried out in the disclosed order, in the opposite order or simultaneously, as desired, without any effect on the result.

The output signal generating step 140 is then carried out, in which output signals 70 and 72, which indicate respectively the water content and the salt concentration in the multiphase fluid flow, are generated on the basis of the measured voltage across the capacitive sensor and the measured current through the capacitive sensor.

In one embodiment, the output signal generating step includes determining a phase difference between the measured voltage and the measured current and generating the first output signal 70 which indicates the salt concentration in the multiphase fluid flow, based on this phase difference.

In one embodiment, the output signal generating step comprises determining an amplitude for the measured current, and generating the second output signal 72 which indicates the water content in the multiphase fluid flow, based on this amplitude.

In one embodiment, the method comprises inputting the first output signal 70 and the second output signal 72 into a control unit 80.

In particular, the output signal generating step can comprise providing amplified and clipped signals from the measured voltage and the measured current, and passing the resulting amplified and clipped signals to a phase-sensitive demodulator.

The voltage measuring step 120 comprises, in one embodiment, using a first transformer, which comprises a primary winding that is connected in parallel to the capacitive sensor, and a secondary winding that is connected to an electric reference point on the one side and to an input for the output circuit 60 on the other side.

The current measuring step 130 comprises, in one embodiment, using a second transformer, which comprise a primary winding that is connected in series to the capacitive sensor and the signal generator 10, and a secondary winding that is connected to the electric reference point on the one side and to an input for the output circuit 60 on the other side.

The reference point may be electric earth or another neutral point, zero point or reference point.

It will be understood that the pipe arrangement illustrated in FIGS. 1-2 and the apparatus illustrated in FIG. 3 or 4 are usable for carrying out the method described with reference to FIG. 5. The fluid flow is passed in this case through a first tubular electrode 6 that is housed within a pipe section 5, whilst the second electrode 7 is arranged in the fluid flow, as explained above.

The apparatus and the method according to the invention are particularly useful in connection with subsea installations for petroleum production.

The above detailed description has been given as an example. Those of skill in the art will see that many variations of and alternatives to the exemplary solutions described in detail will be possible within the scope of the invention as disclosed in the following claims.

The invention claimed is:

1. An apparatus for measuring water content and salt concentration in a multiphase fluid flow in a subsea installation for petroleum production, the apparatus comprising:
   a capacitive sensor located in a pipe section through which the multiphase fluid flow passes;
   a signal generator connected to the capacitive sensor;
   a first measuring transducer for measuring a voltage across the capacitive sensor;
   a second measuring transducer for measuring a current through the capacitive sensor; and
   an output circuit for generating first and second output signals indicative of the salt concentration and water content, respectively, in the multiphase fluid flow based on signals emitted by the first and second measuring transducers;
   wherein the output circuit is configured to determine a phase difference between the signals emitted by the first and second measuring transducers and generate the first output signal based on said phase difference.

2. An apparatus according to claim 1, wherein the output circuit is configured to determine an amplitude of the signal emitted by the second measuring transducer and generate the second output signal based on said amplitude.

3. An apparatus according to claim 2, further comprising a control unit which is configured to receive the first and second output signals, process values for the first and second output signals and communicate the values with an external communication bus.

4. An apparatus according to claim 3, wherein the control unit is configured to control signal parameters for the signal generator.

5. An apparatus according to claim 1, wherein the output circuit comprises:
   a clipping amplifier for each of the signals emitted by the first and second measuring transducers; and
   a phase-sensitive demodulator connected to respective outputs of the clipping amplifiers.

6. An apparatus according to claim 1, wherein the first measuring transducer comprises a first transformer which includes:
   a primary winding connected in parallel to the capacitive sensor; and
   a secondary winding connected between an electric reference point and an input of the output circuit.

7. An apparatus according to claim 1, wherein the second measuring transducer comprises a second transformer which includes:
   a primary winding connected in series to the capacitive sensor and the signal generator; and
   a secondary winding connected between an electric reference point and an input for the output circuit.

8. An apparatus according to claim 1, wherein the capacitive sensor comprises:
   a tubular first electrode which is positioned in said pipe section and through which the fluid flow passes; and
   a second electrode which is positioned in the fluid flow.

9. An apparatus according to claim 8, wherein the second electrode comprises a metal seal penetrator.

10. A method for measuring water content and salt concentration in a multiphase fluid flow in a subsea installation for petroleum production, the method comprising:
    applying a signal from a signal generator to a capacitive sensor located in a pipe section through which the multiphase fluid flow passes;
    measuring a voltage across the capacitive sensor;
    measuring a current through the capacitive sensor; and
    generating first and second output signals indicative of the water content and the salt concentration, respectively, in the multiphase fluid flow based on said voltage across the capacitive sensor and said current through the capacitive sensor;
    wherein the step of generating the first and second output signals comprises determining a phase difference between said voltage and said current and generating the first output signal based on said phase difference.

11. A method according to claim 10, wherein the step of generating the first and second output signals comprises:
determining an amplitude of said current; and
generating the second output signal based on said amplitude.

12. A method according to claim 11, further comprising:
inputting the first and second output signals into a control unit;
processing values for the first and second output signals by means of the control unit; and
providing communication with an external communication bus by means of the control unit.

13. A method according to claim 12, further comprising:
controlling signal parameters for the signal generator by means of the control unit.

14. A method according to claim 10, wherein the step of generating the first and second output signals comprises:
providing amplified and clipped signals from said voltage and said current; and
feeding the resulting amplified and clipped signals to a phase-sensitive demodulator.

15. A method according to claim 10, wherein the step of measuring a voltage across the capacitive sensor comprises using a first transformer which comprises:
a primary winding connected in parallel to the capacitive sensor; and
a secondary winding connected between an electric reference point and an input for the output circuit.

16. A method according to claim 10, wherein the step of measuring a current through the capacitive sensor comprises using a second transformer which comprises:
a primary winding connected in series to the capacitive sensor and the signal generator; and
a secondary winding connected between an electric reference point and an input for the output circuit.

17. A method according to claim 10, further comprising:
passing the fluid flow through a first tubular electrode housed within said pipe section and over a second electrode.

18. A method according to claim 17, wherein the second electrode comprises a metal seal penetrator.

19. An apparatus for measuring water content and salt concentration in a multiphase fluid flow in a subsea installation for petroleum production, the apparatus comprising:
a capacitive sensor located in a pipe section through which the multiphase fluid flow passes;
a signal generator connected to the capacitive sensor;
a first measuring transducer for measuring a voltage across the capacitive sensor;
a second measuring transducer for measuring a current through the capacitive sensor; and
an output circuit for generating first and second output signals indicative of the salt concentration and water content, respectively, in the multiphase fluid flow based on signals emitted by the first and second measuring transducers;
wherein the capacitive sensor comprises a tubular first electrode which is positioned in said pipe section and through which the fluid flow passes, and a second electrode which is positioned in the fluid flow.

20. A method for measuring water content and salt concentration in a multiphase fluid flow in a subsea installation for petroleum production, the method comprising:
applying a signal from a signal generator to a capacitive sensor located in a pipe section through which the multiphase fluid flow passes, said capacitive sensor comprising a tubular first electrode which is housed within said pipe section and a second electrode which is positioned in the fluid flow;
measuring a voltage across the capacitive sensor;
measuring a current through the capacitive sensor; and
generating first and second output signals indicative of the water content and the salt concentration, respectively, in the multiphase fluid flow based on said voltage across the capacitive sensor and said current through the capacitive sensor.

* * * * *